United States Patent [19]

Nakazawa et al.

[11] Patent Number: 4,833,272

[45] Date of Patent: May 23, 1989

[54] PROCESS FOR PREPARING POLYCARBOXYLIC ACID

[75] Inventors: Mikio Nakazawa; Kango Fujitani, both of Uji, Japan

[73] Assignee: New Japan Chemical Co., Ltd., Japan

[21] Appl. No.: 849,105

[22] Filed: Apr. 7, 1986

[30] Foreign Application Priority Data

Apr. 9, 1985 [JP] Japan .................................. 60-76120
Mar. 19, 1986 [JP] Japan .................................. 61-63726

[51] Int. Cl.$^4$ ............................................. C07C 51/16
[52] U.S. Cl. .................................. 562/523; 562/524; 562/525
[58] Field of Search ........................ 562/523, 525, 524

[56] References Cited

FOREIGN PATENT DOCUMENTS 151906 11/1979 Japan .................................... 562/523
510638 8/1939 United Kingdom ................ 562/523

Primary Examiner—Werren B. Lone
Attorney, Agent, or Firm—Larson and Taylor

[57] ABSTRACT

Disclosed is a process for preparing a polycarboxylic acid, the process comprising subjecting a Diels-Alder reaction product of maleic anhydride and a diene and/or the corresponding acid to oxidative cleavage using hydrogen peroxide in the presence of at least one catalyst selected from the group consisting of tungstic acid, molybdic acid and heteropoly acids thereof.

17 Claims, No Drawings

PROCESS FOR PREPARING POLYCARBOXYLIC ACID

This invention relates to a process for preparing a polycarboxylic acid by subjecting a Diels-Alder reaction product of maleic anhydride and a diene and/or the corresponding acid to oxidative cleavage using hydrogen peroxide.

The carboxylic acids prepared by subjecting to oxidative cleavage a Diels-Alder reaction product of maleic anhydride and a diene and/or the corresponding acid are known compounds useful for producing polyimides, polyesters, plasticizers and the like.

Nitric acid oxidation processes have been industrially carried out for manufacturing polycarboxylic acids by oxidatively cleaving the double bond of a Diels-Alder reaction product of maleic anhydride and a diene. For example, it is known to obtain 1,2,3,4-butane-tetracarboxylic acid by oxidizing tetrahydrophthalic anhydride, i.e. a Diels-Alder reaction product, with nitric acid in the presence of an ammonium metavanadate as a catalyst (J. Org. Chem., 30, 1488 (1965), Unexamined Japanese Patent Publication No. 128350/1984, etc.). However, the nitric acid oxidation produces toxic gases such as $NO_x$ gas, and thus requires an expensive trap equipment to prevent the discharge of the pollutants into the atmosphere. Further the nitric acid oxidation gives nitro compounds and the like as by-products and therefore entails a complicated treatment for removing the by-products which would otherwise impair the thermal stability of the contemplated product.

As stated above, the nitric acid oxidation process is unsatisfactory because of the foregoing drawbacks entailed in the oxidative cleavage of Diels-Alder reaction product of maleic anhydride and a diene. Nevertheless, the process has been heretofore used partly because inexpensive nitric acid can be used as an oxidizing agent and partly because any other efficient process has been unavailable.

It is an object of this invention to provide a process for preparing a polycarboxylic acid by subjecting a Diels-Alder reaction product of maleic anhydride and a diene to oxidative cleavage using an inexpensive oxidizing agent in a simple manner without use of expensive equipment such as a device for treating $NO_x$ gas.

This invention provides a process for preparing a polycarboxylic acid, comprising subjecting a Diels-Alder reaction product of maleic anhydride and a diene and/or the corresponding acid to oxidative cleavage using hydrogen peroxide in the presence of at least one catalyst selected from the group consisting of tungstic acid, molybdic acid and heteropoly acids thereof.

We conducted extensive research to develop a process capable of producing a polycarboxylic acid with safety and at low costs and overcoming the drawbacks of conventional nitric acid oxidation processes involving the generation of toxic gases. In the course of our research, we investigated the possibility of using hydrogen peroxide in the process.

Hydrogen peroxide is an aqueous oxidizing agent which can be advantageously used compared with nitric acid because hydrogen peroxide is as cheap as nitric acid as calculated in terms of oxidation equivalent and produces no noxious gas such as $NO_x$, thereby eliminating the need to use equipment for trapping such gas.

Our research revealed that when hydrogen peroxide is used as the oxidizing agent and tungstic acid as the catalyst in the process, the double bond of the Diels-Alder reaction product is oxidatively cleaved, thereby giving the desired polycarboxylic acid.

Reactions for causing the hydrogen peroxide to act on the double bond of maleic acid in the presence of a tungstic acid as the catalyst are disclosed in Unexamined Japanese Patent Publications No. 59,321/1975 and No. 85,119/1977 and DE-OS No. 2,016,668. These known processes are those involving the epoxidation of the double bond of maleic acid and, when required, hydrolysis of the resulting epoxidation product for conversion to a vicinal diol. The publications do not teach that a polycarboxylic acid is obtained by oxidatively cleaving the double bond of the Diels-Alder reaction product with use of hydrogen peroxide and tungstic acid.

Our continued research unexpectedly discovered that when hydrogen peroxide is caused to act on the Diels-Alder reaction product of maleic anhydride and a diene in the presence of a tungstic acid as the catalyst, the double bond of the Diels-Alder reaction product is oxidatively cleaved with high efficiency, giving the corresponding polycarboxylic acid. We also found that the double bond of the Diels-Alder reaction product is oxidatively cleaved when molybdic acid is used as the catalyst.

We also found that when heteropoly acid of tungstic acid or molybdic acid is used as the catalyst, the double bond of the Diels-Alder reaction product can be oxidatively cleaved with high efficiency by hydrogen peroxide, producing the corresponding polycarboxylic acid of high purity in high yields.

This invention has been accomplished based on these novel findings.

The process of this invention employing hydrogen peroxide produces no toxic gas such as $NO_x$ unlike conventional nitric acid oxidation processes, and accordingly does not necessitate the use of equipmnnt for trapping the gas. In addition, hydrogen peroxide is as cheap as nitric acid and therefore is advantageous in terms of production costs. Moreover, the process of the invention gives a polycarboxylic acid of high purity in high yields. Further, it is relatively easy to separate the resulting polycarboxylic acid. Especially when heteropoly acid is used as the catalyst, the polycarboxylic acid thus produced can be easily separated as crystals by a simple procedure of gradually cooling the reaction mixture. After the separation of the crystals, the remaining mother liquor contains a substantial amount of the catalyst which remains almost free from the deactivation, and therefore can be recycled to the reaction. For these reasons, the process of this invention is significantly advantageous from commercial viewpoints.

Examples of dienes useful for forming the Diels-Alder reaction product in this invention are butadiene, piperylene, isoprene, chloroprene, etc. The Diels-Alder reaction between these dienes and maleic anhydride gives tetrahydrophthalic anhydride, 3-methyltetrahydrophthalic anhydride, 4-methyltetrahydrophthalic anhydride, 4chlorotetrahydrophthalic anhydride, etc. Generally, these anhydrides are easily hydrolyzed in the presence of water to give the corresponding acids. The corresponding acids thus produced behave during the oxidation reaction in the same manner as the anhydrides. Accordingly any of the anhydrides, corresponding acids and mixtures thereof can be used as the starting material in the process of the invention.

Examples of catalysts useful in this invention are tungstic acid, molybdic acid and heteropoly acids thereof. The term "heteropoly acid" used herein refers to a polyacid formed from at least two oxyacids. Useful poly acid atoms are tungsten and molybden. Usable hetero-atoms are various as exemplified below. Examples of hetero-atoms in heteropoly acids of tungstic acid are P, As, Si, Ti, Co, Fe, B, V, Be, I, Ni, Ga, etc. Examples of heteropoly acids of tungstic acid are those having the formulas: $H_3[PW_{12}O_{40}]$, $H_3[AsW_{12}O_{40}]$, $H_4[SiW_{12}O_{40}]$, $H_4[TiW_{12}O_{40}]$, $H_5[CoW_{12}O_{40}]$, $H_5[FeW_{12}O']$, $H_5[BW_{12}O_{40}]$, $H_3[VW_{12}O_{40}]$, $H_6[BeW_9O_{31}]$, $H_6[TeW_6O_{24}]$, $H_5[IW_6O_{24}]$, $H_4[NiW_6O_{24}H_6]$, $H_3[GaW_6\ O_{24}H_6]$, $H_6[P_2W_{18}O_{62}]$, $H_6[As_2W_{18}O_{62}]$, $H_7[PW_{11}O_{33}]$, etc. Examples of hetero-atoms in heteropoly acids of molybdic acid are P, As, Si, Ge, Ti, Ce, Th, Mn, Ni, Te, I, Co, Cr, Fe, Ga, etc. Examples of heteropoly acids of molybdic acid are those represented by the formulas: $H_3[PMo_{12}O_{40}]$, $H_3[AsMo_{12}O_{40}]$, $H_4[SiMo_{12}O_{40}]$, $H_4[GeMo_{12}O_{40}]$, $H_4[TiMo_{12}O_{40}]$, $H_8[CeMo_{12}O_{42}]$, $H_8[ThMo_{12}O_{42}]$, $H_7[PMo_{11}O_{39}]$, $H_7[AsMo_{11}O_{39}]$, $H_8[GeMo_{11}O_{39}]$, $H_6[MnMo_9O_{32}]$, $H_6[NiMo_9O_{32}]$, $H_6[TeMo_6O_{24}]$, $H_5[IMo_6O_{24}]$, $H_3[CoMo_6O_{24}H_6]$, $H_3[CrMo_6O_{24}H_6]$, $H_3[FeMo_6O_{24}H_6]$, $H_3[GaMo_6O_{24}H_6]$, $H_4[NiMo_6O_{24}H_6]$, $H_2[P_2Mo_{18}O_{62}]$, $H_6[AsMo_{18}O_{62}]$, etc. Further, mixed coordination heteropoly acids, such as $H_4PMoW_{11}O_{40}$, $H_4PReW_{11}O_{40}$, $H_4PVMo_{11}O_{40}$, $H_5PV_2Mo_{10}O_{40}$, etc. can also be used. The heteropoly acids exemplified above are known compounds. Heteropoly acids containing P or Si as the hetero-atom are preferred because of the ease of preparation or availability. Of such heteropoly acids, 12-tungstophosphoric acid ($H_3PW_{12}O_{40}$), 12-tungstosilicic acid ($H_3SiW_{12}O_{40}$), 12-molybdophosphoric acid ($H_3PMo_{12}O_{40}$) and the like are more preferred.

The tungstic acid, molybdic acid and heteropoly acids thereof to be used as the catalyst in this invention may be employed in the form of a hydrate or in the form of a compound capable of forming the foregoing tungstic acid, molybdic acid or heteropoly acids thereof in the reaction system. Examples of such compounds are salts of alkali metals such as potassium, sodium and the like: salts of heavy metals such as cobalt, nickel, manganese, copper and the like; salts of ammonium ($NH_4$), etc. The tungstic acid and molybdic acid may be used also in the form of oxides, chlorides and sulfides represented by $MO_3$, $MCl_6$ and $MS_3$ (wherein M TM W or Mo), respectively. When the foregoing salts, oxides, chlorides or sulfides are used, it is preferable to incorporate a mineral acid such as phosphoric acid, hydrochloric acid, sulfuric acid or the like into the reaction system to adjust the pH to 4 or less so that the reaction is carried out under such acidic conditions.

The catalysts given above are usable singly or at least two of them can be used in admixture.

Heteropoly acids are desirable in terms of the reactivity while tungstic acid is desired in consideration of the balance between the reactivity and the costs.

The process of this invention may be conducted usually in the following manner. First, a Diels-Alder reaction product and/or the corresponding acid (hereinafter referred to as "substrate") and a catalyst are fed into a reactor, followed by addition of hydrogen peroxide. The mixture is heated with stirring in a solvent.

The concentration of the substrate to be used for the reaction is not specifically limited and can be determined over a wide range insofar as the the substrate can be dissolved in the solvent at the reaction temperature. However, when the polycarboxylic acid produced is separated from the reaction mixture after completion of the reaction by gradually cooling the reaction mixture to crystallize the polycarboxylic acid, the concentration of the substrate is preferably in the range of about 2 to about 70% by weight, more preferably about 30 to about 50% by weight, in view of the amount of the precipitated crystals and the quality of thereof.

The amount of the catalyst to be used in the invention is widely variable insofar as it is an amount effective for achieving the desired catalytic activity. However, from the viewpoints of the reaction rate and cost of the catalyst involved, the amount of the catalyst usually ranges from about 0.1 to about 30% by weight, preferably about 1 to about 10% by weight, based on the substrate.

While the stoichiometric amount of hydrogen peroxide to be used in the reaction of the invention is 4 moles per mole of the substrate, the amount of hydrogen peroxide to be used is preferably about 1.1 to about 1.5 times the stoichiometric amount, i.e., about 4.4 to about 6 moles per mole of the substrate. The concentration of hydrogen peroxide in the reaction mixture can be determined over a wide range. The lower limit of the hydrogen peroxide concentration is in a range sufficient to enable the hydrogen peroxide to restore the lost oxidizing ability of the catalyst which has oxidized the substrate. Even with hydrogen peroxide in a considerably low concentration, the oxidation reaction can proceed although at a reduced reaction rate. The upper limit of the hydrogen peroxide concentration is not specifically limitative and may be at a significantly high level. However, it is advantageous to use hydrogen peroxide in a concentration of about 0.1 mmol/liter to about 12 mols/liter, preferably about 10 mmols/liter to about 8 mols/liter in order to maintain the reaction rate at a reasonable level and to decrease the production costs by using hydrogen peroxide at a relatively low concentration. Hydrogen peroxide is usually fed to the reaction system in the form of an aqueous solution.

As the solvent, water is preferred in this invention. It is also possible to use an organic solvent miscible with water such as alcohols having 1 to 4 carbon atoms, carboxylic acid having 1 to 4 carbon atoms, dioxane, tetrahydrofuran, dimethylformamide and the like. These organic solvents can be used singly or in mixture with water insofar as the mixture retains a homogeneous phase.

The reaction is effected usually at a temperature of about 20° to about 100° C. in view of the reaction rate. When the reaction is conducted at an elevated pressure, the reaction temperature of up to about 150° C. may be employed. Generally, it is preferred to conduct the reaction at a temperature of about 50 to about 130° C. to increase the reaction rate and prevent or inhibit the decomposition of hydrogen peroxide.

The reaction time can be varied depending on the concentration of substrate, catalyst and hydrogen peroxide, reaction temperature and the like but usually ranges from about 1 to about 24 hours.

After completion of the reaction, the polycarboxylic acid produced can be separated from the reaction product by various methods. It is advantageous to gradually cool the reaction mixture to crystallize the polycarboxylic acid. When the heteropoly acid, especially heteropoly acid of tungstic acid, which is very soluble in water or other solvent, is used as the catalyst, there is obtained a clear reaction mixture which, when gradually cooled, causes the polycarboxylic acid present therein to precipitate as plate-like crystals. The crystals thus precipitated can be easily separated by filtration from the mother liquor which contains the catalyst and unreacted substrate as dissolved therein. After separation, the catalyst in the mother liquor remains free from the deactivation and therefore the mother liquor can be recycled to the reaction again. The isolated platelike crystals can be dried as they are, or, when required, washed with water or the like and recrystallized for purification. When tungstic acid or molybdic acidiis used as the catalyst, the catalyst tends to precipitate with the decrease of the hydrogen peroxide concentration. If such precipitation of the catalyst occurs, the precipitated catalyst tends to serve as crystal nuclei to give needle-like or fine plate-like crystals of the polycarboxylic acid formed, causing the reaction mixture to become in a viscous slurry state, and entailing difficulty in separation. Accordingly when tungstic acid or molybdic acid is used as the catalyst, preferably the hydrogen peroxide concentration is retained at a level sufficient to maintain the catalyst in a dissolved state during the separation of the polycarboxylic acid after completion of the reaction, or alternatively the catalyst, when precipitated, is removed by filtration and the like and then the recrystallization is effected, whereby the polycarboxylic acid can be separated with a purity as high as and in a yield as high as when heteropoly acid is used.

The present invention will be described below in greater detail with reference to the following Examples.

EXAMPLE 1

Into a four-necked glass flask equipped with a stirrer were placed 30.4 g (0.2 mole) of tetrahydrophthalic anhydride and 60 g of water. The mixture was heated to 100° C. for 30 minutes to convert the tetrahydrophthalic anhydride into the corresponding acid. The mixture was cooled to 70° C. and 1.0 g of tungstic acid serving as the catalyst was added. Then 15 g of a 60% aqueous solution of hydrogen peroxide was added dropwise. The mixture was heated at 70° C. for 2 hours. To the resulting mixture was added 42 g of a 60% aqueous solution of hydrogen peroxide, and the mixture was heated to 90° C. and subjected to the reaction for 10 hours. For analysis, the water was distilled off from the resulting reaction mixture to obtain 45.8 g of white solids. The solids were found to have a neutralization value of 886. Increase of the free carboxyl group content was found to be 81%, as calculated from the neutralization value. The increase of the free carboxyl group content in this example and other examples that follow was calculated assuming that the difference between the neutralization value of the reaction mixture before the addition of hydrogen peroxide and the neutralization value of the reaction mixture after completion of the reaction corresponds to the increase of the free carboxyl groups formed by the oxidation reaction. The solids were subjected to gas chromatography for analysis with the result that tetrahydrophthalic acid used as the starting material was not detected. The solids thus obtained were recrystallized from water to obtain 1,2,3,4-butane-tetracarboxylic acid. The recrystallization gave 35.2 g of white solids having a neutralization value of 923 (theoretical value 959) and a purity of 96.2% as measured by gas chromatography (yield 75%). The conversion of tetrahydrophthalic acid was 100%.

EXAMPLE 2

The same procedure as in Example 1 was repeated with the exception of using 33.0 g of 3-methyltetrahydrophthalic anhydride in place of tetrahydrophthalic anhydride. The white solids obtained for analysis by distilling off the water were found to have a neutralization value of 834 and weigh 48.4 g. Increase of the free carboxyl group content was 80%. To obtain 1-methyl-1,2,3,4-butane-tetracarboxylic acid, the solids were recrystallized from water, giving 39.2 g of white solids having a neutralization value of 882 (theoretical value 905) in a yield of 78%.

EXAMPLE 3

The same procedure as in Example 1 was repeated with the exception of using 1.0 g of 12-tungstophosphoric acid ($H_3PW_{12}O_{40}$) hydrate, product of Nakarai Kagaku Kabushiki Kaisha, Japan) as the catalyst, giving 40.2 g of solids having a neutralization value of 956. Increase of the free carboxyl group content was 92% and the conversion of tetrahydrophthalic acid was 100%.

EXAMPLE 4

(a) The same procedure as in Example 1 was repeated with the exception of using 1.0 g of molybdic acid as the catalyst. Increase of the free carboxyl group content was 28% and the conversion of tetrahydrophthalic acid was 99.7%. Yield of 1,2,3,4-butane-tetracarboxylic acid was 26%, as determined by gas chromatographic analysis (internal standard method).

(b) The same procedure as in Example 1 was repeated with the exception of using 5.0 g of molybdic acid as the catalyst. Increase of the free carboxyl group content was 86%. Yield of 1,2,3,4-butane-tetracarboxylic acid was 83%, as determined by gas chromatographic analysis (internal standard method).

EXAMPLE 5

Into a four-necked glass flask were placed 30.4 g of tetrahydrophthalic anhydride, 20 g of water and 1.0 g of 12-tungstophosphoric acid ($H_3PW_{12}O_{40}$ hydrate, product of Nakarai Kagaku Kabushiki Kaisha, Japan). Then 51 g of a 60% aqueous solution of hydrogen peroxide was added dropwise over 1 hour to the mixture with stirring while maintaining the temperature of the mixture at 90° C. The resulting reaction mixture was subjected to the reaction at 90° C. for 10 hours, giving a clear reaction mixture. Increase of the free carboxyl group content was 86%.

The reaction mixture thus obtained was cooled to 60° C. and then gradually cooled with stirring to 10 ° C. over a period of 2 hours, crystallizing the desired 1,2,3,4-butane-tetracarboxylic acid as plate-like crystals which were collected by filtration. The crystals thus obtained were dried at 150° C. for 4 hours. The water content in the crystals as measured on filtration based on the loss of weight by drying was 17% by weight. Thus 39.5 g of dried crystals were obtained in a yield of 84%. The crystals had a neutralization value of 951 (theoretical value 959) and were high in purity.

EXAMPLE 6

Into a four-necked glass flask equipped with a stirrer were placed 30.4 g of tetrahydrophthalic anhydride, 60 g of water and 6 g of 12-tungstosilicic acid ($H_4SiW_{12}O_{40}\cdot24H_2O$, product of Nakarai Kagaku Kabushiki Kaisha), and the mixture was maintained at 90° C. Then 57 g of a 60% aqueous solution of hydrogen peroxide was added dropwise to the mixture with stirring over 1 hour. The mixture was subjected to reaction at 90° C. for 10 hours. Increase of the free carboxyl group content was 79%. Gas chromatographic analysis revealed that none of the tetrahydrophthalic anhydride used and the corresponding acid were detected in the reaction mixture. Yield of the desired 1,2,3,4-butane-tetracarboxylic acid was 74% as determined by gas chromatographic analysis (internal standard method).

EXAMPLE 7

The same reaction in Example 6 was repeated with the exception of using 3 g of 12-molybdophosphoric acid ($H_3PMo_{12}O_{40}$ hydrate, product of Nakarai Kagaku Kabushiki Kaisha) in place of 6 g of 12-tungstosilicic acid. Increase of the free carboxyl group content was 90%. None of the tetrahydrophthalic acid used and the corresponding acid were detected in the reaction product by gas chromatography. Yield of the desired 1,2,3,4-butane-tetracarboxylic acid was 85% as determined by gas chromatographic analysis (internal standard method).

We claim:

1. A process for preparing a polycarboxylic acid comprising subjecting a Diels-Alder reaction product of maleic anhydride or maleic acid or mixture thereof and a diene selected from the group consisting of butadiene, piperylene, isoprene or chloroprene to oxidative cleavage using hydrogen peroxide at a temperature of about 20° to 150° C. in the presence of at least one catalyst selected from the group consisting of tungstic acid, molybdic acid, heteropoly acid of tungstic acid, heteropoly acid of molybdic acid and mixed coordination heteropoly acids, the heteropoly acid of tungstic acid being a heteropoly acid of tungstic acid wherein the hetero-atom is one selected from the group consisting of P, As, Si, Ti, Co, Fe, B, V, Be, I, Ni and Ga; and the heteropoly acid of molybdic acid being a heteropoly acid of molybdic acid wherein the hetero-atom is one selected from the group consisting of P, As, Si, Ge, Ti, Ce, Th, Mn, Ni, Te, I, Co, Cr, Fe and Ga; and the mixed coordination heteropoly acids being selected from the group consisting of $H_4PMoW_{11}O_{40}$, $H_4PReW_{11}O_{40}$, $H_4PVMo_{11}O_{40}$ and $H_5PV_2Mo_{10}O_{40}$.

2. A process according to claim 1 wherein the Diels-Alder reaction product of maleic anhydride and/or the corresponding acid is used in a concentration of about 2 to about 70% by weight.

3. A process according to claim 1 wherein the Diels-Alder reaction product of maleic anhydride and/or the corresponding acid is used in a concentration of about 30 to about 50% by weight.

4. A process according to claim 1 wherein the catalyst is tungstic acid.

5. A process according to claim 1 wherein the catalyst is molybdic acid.

6. A process according to claim 1 wherein the catalyst is a heteropoly acid of tungstic acid wherein the hetero-atom is one selected from the group consisting of P, As, Si, Ti, Co, Fe, B, V, Be, I, Ni and Ga.

7. A process according to claim 1 wherein the catalyst is a heteropoly acid of molybdic acid wherein the hetero-atom is one selected from the group consisting of P, As, Si, Ge, Ti, Ce, Th, Mn, Ni, Te, I, Co, Cr, Fe and Ga.

8. A process accordnng to claim 1 wherein the catalyst is a heteropoly acid of tungstic acid wherein the hetero-atom is P or Si.

9. A process according to claim 1 wherein the catalyst is a heteropoly acid of molybdic acid wherein the hetero-atom is P or Si.

10. A process according to claim 1 wherein the catalyst is 12-tungstophosphoric acid, 12-tungstosilicic acid or 12-molybdophosphoric acid.

11. A process according to claim 1 wherein the catalyst is used in an amount of about 0.1 to about 30% by weight based on the Diels-Alder reaction product of maleic anhydride and/or the corresponding acid.

12. A process according to claim 1 wherein the catalyst is used in an amount of about 1 to about 10% by weight based on the Diels-Alder reaction product of maleic anhydride and/or the corresponding acid.

13. A process according to claim 1 wherein the amount of hydrogen peroxide is about 1.1 to about 1.5 times the stoichiometric amount based on the Diels-Alder reaction product of maleic anhydride and/or the corresponding acid.

14. A process according to claim 1 wherein hydrogen peroxide is used in the reaction system in a concentration of about 0.1 mmol/liter to about 12 mols/liter.

15. A process according to claim 1 wherein the oxidative cleavage is conducted in a solvent, the solvent being water, an organic solvent miscible with water or a uniform mixture of water and an organic solvent miscible with water.

16. A process according to claim 1 wherein the oxidative cleavage is carried out at a temperature of about 50° to about 130° C.

17. A process according to claim 1 wherein the catalyst is a mixed coordination heteropoly acid selected from the group consisting of $H_4PMoW_{11}O_{40}$, $H_4PReW_{11}O_{40}$, $H_4PVMo_{11}O_{40}$, and $H_5PV_2Mo_{10}O_{40}$.

* * * * *